(12) United States Patent
Kermani

(10) Patent No.: US 6,872,298 B2
(45) Date of Patent: Mar. 29, 2005

(54) DETERMINATION OF SAMPLE VOLUME ADEQUACY IN BIOSENSOR DEVICES

(75) Inventor: Mahyar Z. Kermani, Pleasanton, CA (US)

(73) Assignee: LifeScan, Inc., Milpitas, CA (US)

(*) Notice: Subject to any disclaimer, the term of this patent is extended or adjusted under 35 U.S.C. 154(b) by 304 days.

(21) Appl. No.: 09/988,495

(22) Filed: Nov. 20, 2001

(65) Prior Publication Data

US 2003/0094383 A1 May 22, 2003

(51) Int. Cl.[7] .............................................. G01N 27/327
(52) U.S. Cl. ................ 205/777.5; 204/400; 204/403.01; 204/403.14; 324/662; 324/663; 324/667; 324/671; 324/686
(58) Field of Search ............................. 205/777.5, 778; 324/662, 663, 667, 671, 677, 678, 686, 425–437, 658, 664; 204/400–420

(56) References Cited

U.S. PATENT DOCUMENTS

| | | | |
|---|---|---|---|
| 5,628,890 A | | 5/1997 | MediSense, Inc. |
| 6,544,475 B1 | * | 4/2003 | Douglas et al. ............... 422/61 |
| 6,616,819 B1 | | 9/2003 | Liamos et al. |

FOREIGN PATENT DOCUMENTS

| | | | |
|---|---|---|---|
| EP | 0438159 A | 7/1991 | |
| EP | 0504637 A | 9/1992 | |
| WO | WO 8703095 A1 * | 5/1987 | ......... G01N/33/566 |
| WO | WO 9739343 A1 * | 10/1997 | .......... G01N/27/22 |
| WO | WO 98/35225 | 8/1998 | ......... G01N/27/327 |
| WO | WO 99/32881 | 7/1999 | .......... G01N/27/26 |
| WO | WO 99/45387 | 9/1999 | ......... G01N/33/487 |
| WO | WO 99/56613 | 11/1999 | ............ A61B/5/00 |
| WO | WO 00/20626 | 4/2000 | ............ C12Q/1/00 |

* cited by examiner

*Primary Examiner*—Alex Noguerola
(74) *Attorney, Agent, or Firm*—Carol M. LaSalle; Bozicevic, Field & Francis, LLP

(57) ABSTRACT

Systems and methods are provided for determining whether a volume of biological sample is adequate to produce an accurate analyte concentration measurement. Certain such systems and methods provide the additional function of compensating for a sample volume determined to be less than adequate in order to proceed with an accurate analyte concentration measurement. The present invention is employed with a biosensor, such as an electrochemical test strip to which the sample volume of biological solution is deposited, and a meter configured to receive such test strip and to measure the concentration of selected analytes within the biological sample.

47 Claims, 3 Drawing Sheets

DETERMINATION OF SAMPLE VOLUME ADEQUACY IN BIOSENSOR DEVICES

FIELD OF THE INVENTION

The field of this invention is the electrochemical determination of analyte in biological fluids, particularly the electrochemical determination of the adequacy of the volume of the biological fluid sample to be tested for analyte concentration.

BACKGROUND OF THE INVENTION

Analyte concentration determination in biological fluids, e.g., blood or blood-derived products such as plasma, is of ever increasing importance to today's society. Such assays find use in a variety of applications and settings, including clinical laboratory testing, home testing, etc., where the results of such testing play a prominent role in the diagnosis and management of a variety of disease conditions. Common analytes of interest include glucose for diabetes management, cholesterol for monitoring cardiovascular conditions, and the like. In response to this growing importance of analyte concentration detection, a variety of analyte detection protocols and devices for both clinical and home use have been developed.

One type of method that is employed for analyte detection is an electrochemical-based method. In such methods, an aqueous liquid sample is placed into a reaction zone in an electrochemical cell made up of at least two electrodes, i.e., a counter/reference electrode and a working electrode, where the electrodes have an impedance which renders them suitable for amperometric measurement. The component to be analyzed, e.g., an analyte, is allowed to react directly with an electrode, or directly or indirectly with a redox reagent to form an oxidisable (or reducible) substance in an amount corresponding to the concentration of the component to be analyzed, i.e., analyte. The quantity of the oxidisable (or reducible) substance present is then estimated electrochemically and related to the amount of analyte present in the initial sample.

Commonly, the electrochemical cell is in the form of a disposable test strip on which the biological sample is deposited and which is receivable within a meter by which the electrochemical analyte concentration is made. Examples of assay systems that employ these types of test strips, often referred to as biosensors, and meters may be found in U.S. Pat. Nos. 5,942,102, 6,174,420 B1 and 6,179,979 B1, the disclosures of which are herein incorporated by reference. With these systems, determination of the concentration of an analyte in a biological sample first involves obtaining a biological sample and bringing that sample into contact with a reaction area of the test strip so that the biological sample, and more particularly the analyte of interest or derivative thereof, may react with the chemistry, e.g., the testing reagent(s), associated with the reaction area. In order to obtain an accurate measurement of the particular analyte(s) of interest, a minimum sample volume must be applied to the reaction area. It is not uncommon for an inadequate amount of sample volume to be provided, often due to user error or patient inexperience or misjudgment. Inaccurate measurements can result in a misdiagnosis or improper treatment, such as administering an inappropriate dosage of a drug, patient non-compliance, etc. Such can result in serious and even life-threatening consequences for those whose lives depend on frequent monitoring of an analyte in their body, for example, diabetics.

One approach to ensuring an adequate biological sample volume is to over-saturate or use a greater volume of sampled fluid than is necessary to fill the reaction area of the test strip. A disadvantage of using an unnecessarily large volume of sampled fluid, a blood sample in particular, is the need to draw a greater volume of blood sample from the patient. This requires use of a blood sample volume which is rather large, thus necessitating use of a larger diameter needle and/or deeper penetration into the skin. These factors can increase the discomfort and pain felt by the patient, and may be difficult to achieve for those individuals whose capillary blood does not readily express. As this sampling process may be repeated frequently within a single day, for many diabetics, for example, an increase in pain quickly becomes less tolerable or intolerable all together.

Some analyte detection biosensors have been developed to provide visual confirmation of the adequacy of sample volume, however, this feature does not exclude potential error by the patient in judging the adequacy of the sample's volume, e.g., diabetics may experience deteriorated vision. Certain other analyte determination biosensors do provide user-independent means for determining the adequacy of the sample volume. Examples of such biosensors are disclosed in U.S. Pat. Nos. 5,628,890 and 5,650,062 and PCT Patent Application Publication No. WO 99/32881 (PCT Patent Application No. PCT/US98/27203). In particular, the '881 publication describes an electrochemical glucose monitoring system which attempts to determine the adequacy of a volume of sample applied to a biosensor by applying a low-level AC voltage signal (without a DC voltage offset) at a known frequency to the biosensor and then measuring both the real component and the imaginary component of the resulting impedance. These impedance values are then compared to a look-up table in the microprocessor's program memory. The accuracy of this method may be additionally questionable considering that this system is dependent on blood hematocrit levels and environmental temperature variations.

Another disadvantage of the technique disclosed in the '881 publication is that the analyte measurement test must be aborted if the sample volume is determined to be inadequate, i.e., a "go-no-go" situation. This results in the need to take yet another sample from the patient which, as mentioned above, is inconvenient and may be very painful to the patient, likely resulting in patient non-compliance in his or her medication regime. Additionally, the test must be repeated resulting in the waste of test strips and increasing the cost of the procedure.

As such, there is continued interest in the identification of new techniques for accurately and precisely measuring the adequacy of the volume of the sample used for electrochemical analyte concentration determination. Of particular interest would be the development of devices and methods that can very accurately and expeditiously determine the adequacy of the volume of sample. It would be additionally beneficial to develop such a sample volume adequacy determination device and technique in which a determination that a sample volume is inadequate does not require abortion of the analyte concentration measurement test. Ideally, this device and technique would compensate for the less than optimal sample volume and provide an accurate measurement without having to provide a new sample or to conduct a new test.

SUMMARY OF THE INVENTION

The present invention provides methods, systems and devices for measuring the volume of biological sample and determining whether such volume is adequate to produce an accurate measurement of at least one selected characteristic of the biological sample, such as the concentration of an analyte contained therein. Certain such methods, systems and devices provide the additional function of compensating for a sample volume determined to be less than adequate in order to proceed with a measurement procedure.

The present invention is employed with a biosensor, such as an electrochemical test strip to which the sample volume of biological solution is deposited, and a meter configured to receive such test strip and to measure the concentration of selected analytes within the biological sample. The electrochemical test strip, as will be more fully described below, includes an electrochemical cell comprised of opposing electrodes between which a reaction zone is defined for receiving the biological sample, wherein the reaction zone has a defined thickness and volume.

When sufficient voltage is applied to an electrochemical cell, the cell becomes charged and an electrochemical reaction will occur within the charged cell. As a consequence, charge flows to the electrodes of an electrical cell. The electrode-solution interface is analogous to that of a capacitor. The ratio of this charge to the voltage determines the capacitance of the electrode-solution interface. Since the total charge is due to the charging of the double layer and to the electrochemical reaction, two distinct capacitance components, Cdl and Cs, respectively, contribute to the total or equivalent capacitance of the cell (see Bard, A. J. and Faulkner, L. R., Electrochemical Methods, 1980).

The inventor has discovered that the equivalent capacitance of an electrochemical cell is the most relevant factor in precisely determining sample volume, as the equivalent cell capacitance is linearly proportional to the amount of surface area of the cell electrodes in contact with the sample (the "covered cell area"), and thus, is linearly proportional to the volume of the sample within the cell, i.e., between the electrodes.

The inventor has also discovered that the electrochemical cell can be used as a part of an oscillator circuit having an oscillation period (or the inverse of the oscillation frequency) proportional to the cell equivalent capacitance produced by the electrochemical cell when a DC voltage is applied to the cell. Thus, a feature of the present invention is to provide an oscillator operatively coupled to the electrochemical cell such that an oscillation is produced having a period proportional to the equivalent capacitance, to measure this period and then to derive the equivalent capacitance from the measured period.

Generally described, the systems of the present invention may include the following components: a voltage supply configured for applying a voltage to the electrochemical cell to charge the cell; means for receiving voltage signal from the charged cell and converting such voltage signal to an oscillating signal; means for deriving the capacitance of the cell from the oscillating; means for deriving the surface area of the cell covered by the biological sample from the cell capacitance; and means for deriving the volume of the biological sample from the covered cell surface area. Certain systems further include means for determining whether the sample volume is adequate for making an accurate measurement of one or more selected characteristics of the biological sample, including but not limited to the concentration of one or more selected analytes within the biological sample. Certain of these systems further include means for compensating for an inadequate sample volume while the selected characteristic of the biological sample.

In one embodiment, the subject system includes a voltage supply configured for applying a first voltage to said electrochemical cell; means for measuring a second voltage generated by said cell when said first voltage is applied to said cell; means for converting said second voltage into a oscillating voltage; means for deriving the capacitance of said cell from said oscillating voltage; means for deriving the surface area of said cell covered by said biological sample from said cell capacitance; and means for deriving the volume of said biological sample from said surface area.

The above mentioned means of the subject systems include electronic components and/or circuitry intended to be used with and electronically coupled to a biosensor, e.g., an electrochemical measurement cell in the form of, e.g., a disposable test strip, into which the sampled solution to be tested is deposited or is drawn by a capillary action. Most typically, such electronic circuitry is incorporated into a meter or other automated device configured to receive and operatively engage with such electrochemical cell, e.g., a disposable test strip, and to measure one or more physical or chemical characteristics of a biological sample held within the electrochemical cell. Such electronic circuitry can be implemented using available commercial parts or can be implemented as a part of an ASIC (Application Specific Integrated Circuit). Most typically, such characteristics include the concentration of one or more target analytes within the biological sample. Such electronic circuitry may comprise discrete electronic components, e.g., a voltage supply, and/or integrated circuits having multiple circuit elements and/or semiconductor devices, e.g., a microprocessor suitably programmed to execute certain steps or functions of the subject methods based on certain signal or data inputs received from the electrochemical cell.

The subject circuitry may further include a display device or unit for displaying selected empirical or symbolic data, information or outputs supplied by the control device or microprocessor. Such data, information or outputs may include, but are not limited to, measured or derived values of selected input and output signals, impedance factors, sample volume size, volume adequacy/inadequacy indicator icons, inadequate volume compensation factors, concentrations of analytes of interest, biological sample versus control sample indicator icons, calibration results, etc.

In certain embodiments, the systems of the present invention include such electronic circuitry and an automated measurement device or meter, wherein the electronic circuitry is completely structurally and functionally integral with the automated measurement device. For example, one such embodiment includes a meter for receiving an electrochemical cell configured for receiving a biological sample and having a capacitance created by the biological sample when a voltage is applied to the electrochemical cell. The system further includes a DC voltage supply configured to be electrically connectable to the electrochemical cell for charging the electrochemical cell to create a cell capacitance, and an electronic circuit integrally configured with the meter and configured to be electronically connectable to the electrochemical cell. The circuit includes an oscillator circuit configured to receive a voltage input signal resulting from the charging and discharging of the electrochemical cell and also configured to convert the voltage input signal to an oscillating voltage output signal, wherein the period of oscillating voltage output signal is proportional to the capacitance of the cell.

The present invention also includes methods for determining the adequacy of the volume of a biological sample to be used for determining the concentration of one or more selected analytes within the biological sample deposited or transferred to a biosensor. The oscillator charges and discharges the cell capacitance and, therefore, its frequency or period of oscillation depends on the magnitude of the cell capacitance. The cell charge and discharge voltage is controlled such that a net DC voltage is applied to the cell. Next, the equivalent cell capacitance of the biosensor is determined from this oscillating voltage. From the equivalent capacitance, the surface area of the portion of the biosensor in contact with the biological sample ("the covered cell area") is then used to derive the volume of the biological sample within the biosensor. Upon a determination that the sample volume is sufficient to proceed with the measurement test, the targeted characteristic, e.g., analyte concentration, is measured. On the other hand, if it is determined that the sample volume is inadequate, the subject methods may further include compensating for such inadequate sample volume during the measurement process. Inadequate volume compensation involves determining the ratio of the equivalent cell capacitance of the biosensor containing the actual sample volume to the cell capacitance of the biosensor when its entire available volume is filled.

While the subject systems and methods may be used to determine the sample volume of different biological samples, such as urine, tears, saliva, and the like, they are particularly suited for use in determining the sample volume of blood or blood fractions and the like. Furthermore, while the subject systems and methods for determining the sample volume in preparation for measuring a variety of physical and chemical characteristics of the sample, they are particularly useful in preparation for measuring the concentration of selected analytes within the sample.

These and other objects, advantages, and features of the invention will become apparent to those persons skilled in the art upon reading the details of the methods and systems of the present invention which are more fully described below.

DETAILED DESCRIPTION OF THE PREFERRED EMBODIMENTS

Figure 1:
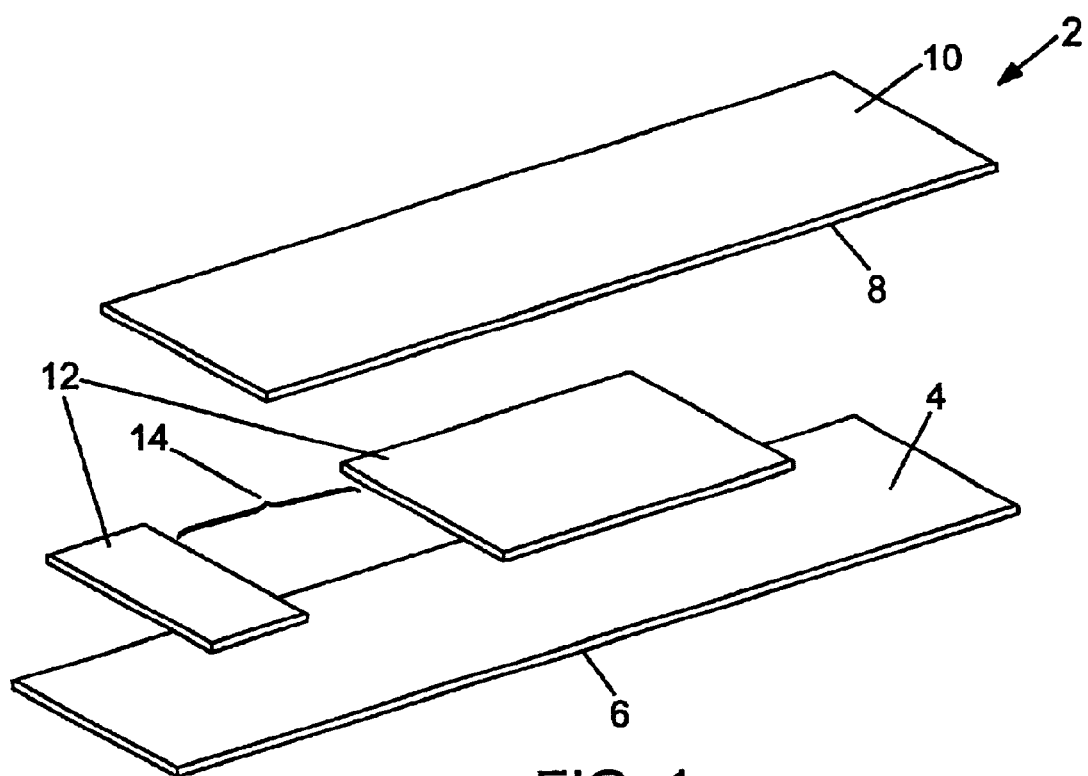
FIG. 1 is an exploded view of an exemplary conventional electrochemical test strip for electrochemical analyte concentration determination, which is usable with the present invention.

The present invention provides systems and methods for determining the volume of a biological sample for purposes of measuring a selected characteristic of the sample, e.g., analyte concentration, and determining whether such volume is adequate to produce an accurate measurement of such selected characteristic. Certain embodiments of the systems and methods of the present invention provide the additional function of compensating for a sample volume determined to be less than adequate in order to provide an accurate analyte concentration measurement.

Before the present invention is described in further detail, it is to be understood that this invention is not limited to the particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, a limited number of the exemplary methods and materials are described herein.

It must be noted that as used herein and in the appended claims, the singular forms "a", "an", and "the" include plural referents unless the context clearly dictates otherwise.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publications provided may differ from their actual publication dates, which may need to be independently confirmed.

Definitions

The term "double layer" as used herein refers to the whole array of charged species and oriented dipoles existing at the interface between an electrode surface and a solution, e.g., a sample of a biological solution, in contact with the electrode surface when a voltage is applied to the electrode.

The term "double layer capacitance," $C_{dl}$, as used herein means the capacitance contributed by the charging of the double layer of the electrode-solution interface.

The term "Faradaic capacitance," Cs, as used herein refers to the pseudo-capacitance component due to the electrochemical reaction process that occurs on the electrode surface.

The term "Faradic current," $I_F$, as used herein means the current or electron transfer that occurs at the surface of an electrode to which a voltage has been applied.

The term "equivalent cell capacitance," C, when used herein in reference to an electrochemical cell means the total equivalent capacitance across the electrochemical cell, which results when a voltage has been applied to the electrochemical cell. The equivalent cell capacitance is dominated by the double layer capacitance and the Faradaic capacitance.

The term "equivalent cell resistance," R, as used herein in reference to an electrochemical cell means the total equivalent resistance across the electrochemical cell, which results when a voltage has been applied to electrochemical cell.

The "equivalent cell impedance," Z, as used interchangeably herein in reference to an electronic circuit or component, e.g., an electrochemical cell, means the total impedance of the circuit including but not necessarily limited to the combination of the equivalent cell capacitance and the equivalent cell resistance, which results when a voltage has been applied to the electrochemical cell.

The present invention will now be described in detail. In further describing the present invention, exemplary electrochemical biosensors, usable with the systems and employable by the methods of the present invention, will be described first, followed by a detailed description of the subject systems and the subject methods, as well as a description of the subject kits that include the subject systems for use in practicing the subject methods. In the following description, the present invention will be described in the context of analyte concentration measurement applications; however, such is not intended to be limiting and those skilled in the art will appreciate that the subject systems and methods are useful in measurement of other physical and chemical characteristics of biological substances such as blood coagulation time and measuring blood cholesterol.

Electrochemical Biosensors

As summarized above, the invention provides systems and methods for measuring the volume of a sample of biological material used for analyte concentration measurement and determining whether such volume is adequate to produce an accurate analyte concentration measurement. These methods and systems are usable with a biosensor, more particularly an electrochemical cell-based biosensor, into which the sampled biological material is deposited or transferred. There are varying designs of electrochemical cell-based biosensors. The most common of these designs employed in the field of analyte concentration monitoring include test strip configurations, such as those disclosed in copending U.S. Pat. No. 6,193,873 and in copending U.S. patent application Ser. Nos. 09/497,304; 09/497,269; 09/736,788 and 09/746,116, the disclosures of which are herein incorporated by reference. Such test strips are used with meters configured for electrochemical measurements, such as those disclosed in the above-identified patent references.

Electrochemical biosensors other than test strips may also be suitable for use with the present invention. For example, the electrochemical cell may have a cylindrical configuration wherein a core electrode is co-axially positioned within a second tubular electrode. Such electrochemical cell configurations may be in the form of micro-needles and, as such, are either integral within the needle structure for in situ (e.g., typically under the skin surface) measurements or otherwise in physical or fluid communication with a micro-needle structure. Examples of such micro-needle are disclosed in co-pending U.S. patent application Ser. Nos. 09/878,742 and 09/879,106 filed on Jun. 12, 2001 now U.S. Pat. No. 6,501,976, hereby incorporated by reference. For purposes of this disclosure, the subject devices will be described in use with electrochemical cells in test strip configurations; however, those skilled in the art will appreciate that the subject devices may be used with any suitable electrochemical cell configuration, including micro-needle configurations.

The type of electrochemical measurement that is made may vary depending on the particular nature of the assay and the meter with which the electrochemical test strip is employed, e.g., depending on whether the assay is coulometric, amperometric or potentiometric. The electrochemical cell will measure charge in a coulometric assay, current in an amperometric assay and potential in a potentiometric assay. For purposes of this disclosure, the present invention will be described in the context of amperometric assays; however, the subject devices may be employed with any type of assay and electrochemical measurement.

Generally, in any configuration, an electrochemical cell includes at least two electrodes spaced-apart in either a facing arrangement or in a side-by-side arrangement in the same plane. In the first arrangement, the electrodes are separated by a thin spacer layer, which defines a reaction area or zone, or chamber into which a biological sample is deposited or transferred for analyte concentration measurement. In the side-by-side configuration, the electrodes are in a chamber with a defined thickness and volume. Present in the reaction area or chamber, i.e., coated on one or more of the facing surfaces of the electrodes, are one or more redox reagents selected to chemically react the target analyte(s). Such redox reagents typically comprise an enzyme and a mediator.

A representation of an exemplary conventional electrochemical test strip 2 suitable for use with the present invention is provided in the exploded view of FIG. 1. Test strip 2 is made up of a two electrodes 4, 8 separated by a spacer layer 12 which has a cutaway section that defines the reaction zone or area 14. Generally, the electrodes 4, 8 are configured in the form of elongated rectangular strips each having a length in the range from about 2 to 6 cm, usually from about 3 to 4 cm, having a width in the range from about 0.3 to 1.0 cm, usually from about 0.5 to 0.7 cm, and having a thickness in the range from about 0.2 to 1.2 mm, and usually from 0.38 to 0.64 mm.

The surfaces of electrodes 4, 8 that face the reaction area in the strip is made of a conductive material, preferably a metal, where metals of interest include palladium, gold, platinum, silver, iridium, carbon, doped indium tin oxide, stainless steel and the like. The outside surfaces 6, 10 of electrodes 4, 8 are made of an inert support or backing material. Any suitable inert backing material may be used with electrodes 4, 8, where typically the material is a rigid material that is capable of providing structural support to the electrode and, in turn, the electrochemical test strip as a whole. Such suitable materials include plastics, e.g., PET, PETG, polyimide, polycarbonate, polystyrene, silicon, ceramic, glass, and the like. Electrodes 4, 8 and test strip 2 may be fabricated using any of various manufacturing techniques known to those skilled in the relevant art. As described above, a thin spacer layer 12 is positioned or sandwiched between electrodes 4, 8. The thickness of spacer layer 12 generally ranges from about 1 to 500 mm, and usually from about 50 to 150 mm. Spacer layer 12 may be fabricated from any convenient material, where representative suitable materials include PET, PETG, polyimide, polycarbonate and the like. The surfaces of spacer layer 12 may be treated so as to be adhesive with respective electrodes 4, 8 and thereby maintain the structure of the electrochemical test strip 2.

Spacer layer 12 is cut so as to provide a reaction zone or area 14 having any appropriate shape including circular, square, triangular, rectangular, or irregular shaped reaction areas, etc. The top and bottom of the reaction zone 14 is defined by the facing surfaces of electrodes 4, 8 while spacer layer 12 defines the side walls of the reaction area 14. The volume of the reaction area ranges from at least about 0.1 to 10 ml, usually from about 0.2 to 5.0 μL and more usually from about 0.3 to 1.6 μL.

Present in the reaction area 14 is a redox reagent system, which reagent system provides for the species that is detected by the electrode and therefore is used to derive the concentration of analyte in a biological sample. The redox reagent system present in the reaction area typically includes at least an enzyme(s) and a mediator. In many embodiments, the enzyme member(s) of the redox reagent system is an enzyme or plurality of enzymes that work in concert to oxidize the analyte of interest. In other words, the enzyme component of the redox reagent system is made up of a single analyte oxidizing enzyme or a collection of two or more enzymes that work in concert to oxidize the analyte of interest. Typical enzymes of interest include oxidoreductases, hydrolases, transferases and the like; however, the specific enzyme present in the reaction area depends on the particular analyte for which the electrochemical test strip is designed to detect. Where the analyte of interest is glucose, for example, suitable enzymes include glucose oxidase, glucose dehydrogenase (either b-nicotineamide adennine dinucleotide based (NAD) or 4,5-Dihydro-4,5-dioxo-1H-pyrrolo[2,3-f]quinoline-2,7,9-tricarboxylic acid based (PQQ)). Where the analyte is cholesterol, suitable enzymes include cholesterol esterase and cholesterol oxidase. For other analytes, enzymes including but not limited to lipoprotein lipase, glycerol kinase, glycerol-3-phosphate oxidase, lactate oxidase, lactate dehydrogenase, pyruvate oxidase, alcohol oxidase, bilirubin oxidase, uricase, and the like may be used.

The second component of the redox reagent system is a mediator component, which is made up of one or more mediator agents. A variety of different mediator agents are known in the art and include: ferricyanide, phenazine ethosulphate, phenazine methosulfate, pheylenediamine, 1-methoxy-phenazine methosulfate, 2,6-dimethyl-1,4-benzoquinone, 2,5-dichloro-1,4-benzoquinone, ferrocene derivatives, osmium bipyridyl complexes, ruthenium complexes and the like. In those embodiments where glucose in the analyte of interest and glucose oxidase or glucose dehydrogenase is the enzyme components, mediator of particular interest is ferricyanide. Other reagents that may be present in the reaction area include buffering agents, e.g., citraconate, citrate, phosphate, "Good" buffers and the like.

The redox reagent system is generally present in dry form. The amounts of the various components may vary, where the amount of enzyme component typically ranges from about 0.1 to 20% by weight.

Figure 2:
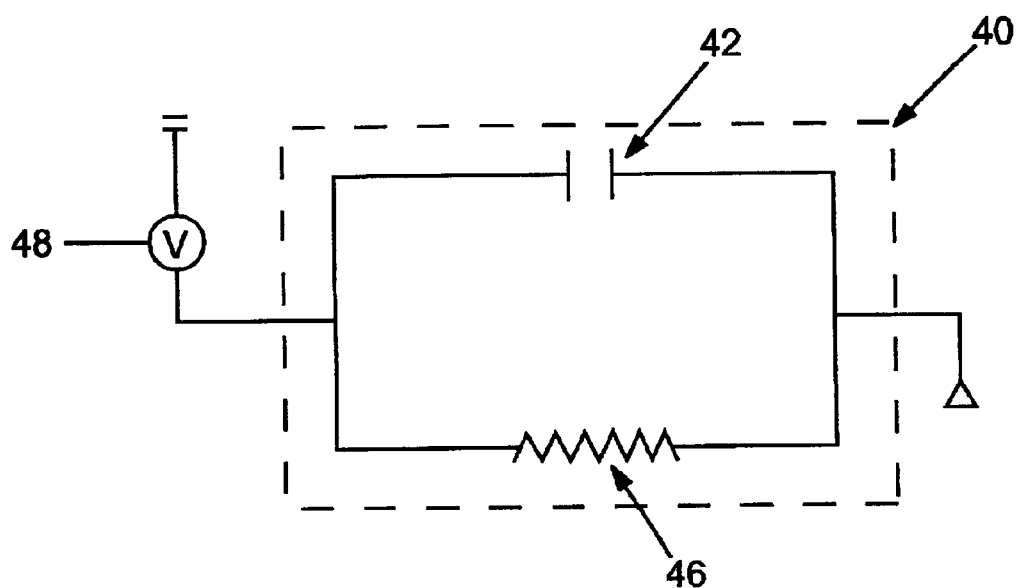
FIG. 2 is a schematic illustration of a circuit representative of the equivalent cell impedance of the test strip of FIG. 1.

For purposes of understanding the following descriptions of the subject systems and methods, a simplified model of an impedance circuit 40 of the electrochemical cell of the test strip of FIG. 1 is provided in FIG. 2. Impedance circuit 40 is representative of the impedance factors of the test strip when containing a sample of biological solution and having a voltage applied to it by voltage supply 48. When a DC voltage is applied to the cell, impedance circuit 40 comprises equivalent cell capacitance (C) 42, which includes the double layer ($C_{dl}$) and the Faradaic ($C_S$) capacitances, and the equivalent cell resistance (R) 46 of the electrochemical cell.

Systems of the Present Invention

The systems of the present invention include electronic circuitry configured to be electronically coupled to a biosensor, e.g., an electrochemical measurement cell in the form of a disposable test strip as described above with respect to FIG. 1, into which the sampled biological solution to be tested is deposited or transferred. Typically, such electronic circuitry is integrally configured within an electrochemical meter of the types referenced above. The systems of the present invention then include such a meter and the integrally configured subject devices.

Figure 3:
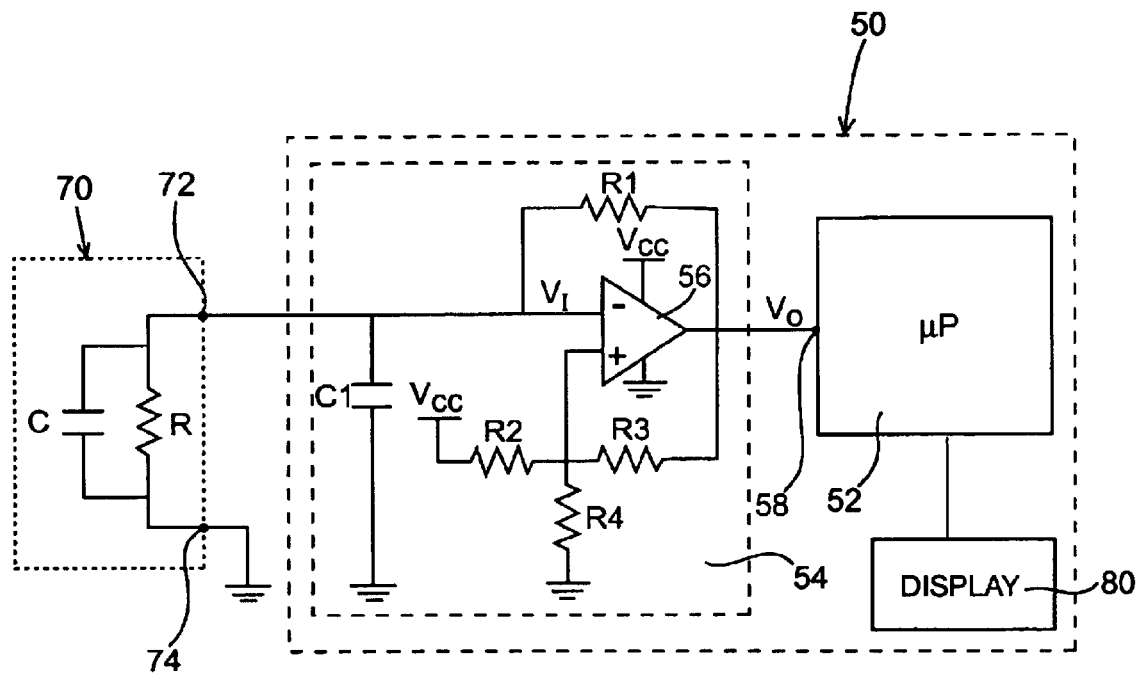
FIG. 3 is a part schematic and a part block diagram of an electronic circuit of an embodiment of a system of the present invention operatively coupled to an electrochemical biosensor for determining the adequacy of a sample volume according to the present invention.

Referring to FIG. 3, there is provided a schematic/block diagram of an exemplary electronic circuit 50 of a system of the present invention electronically coupled to a biosensor 70, and in particular, to the electrodes (not shown) of the electrochemical cell within a test strip as described above. The parallel capacitor C and resistor R illustrated within biosensor 70 respectively represent the equivalent capacitance and the equivalent resistance of the electrochemical cell, and collectively representing the impedance of biosensor 70. Circuit 50 includes a microprocessor 52 electrically coupled to the oscillator circuit 54. Biosensor 70 is electrically coupled to oscillator circuit 54 via terminals 72 and 74. The voltage applied to the cell is illustrated in FIG. 4 with the average DC voltage identified by reference number 60.

Figure 4:
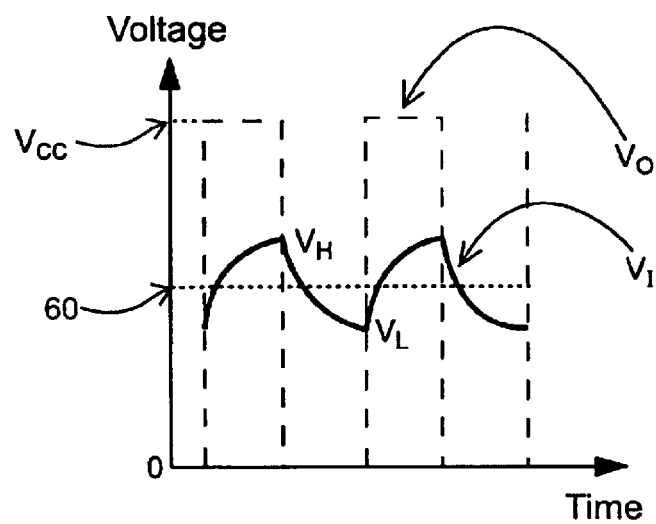
FIG. 4 is a graph illustrating the input voltage ($V_I$) waveform applied to an electrochemical cell of a test strip and oscillator output voltage ($V_O$) waveform from the electronic circuit of FIG. 3 and in accordance with the present invention.

Circuit 54 generally operates as oscillator circuit which provides an output voltage $V_O$ having a rectangular shape waveform, as illustrated in FIG. 4. Circuit 54 includes a power supply $V_{CC}$, a feedback resistor R1, a capacitor C1 and a Schmidt trigger circuit which includes operational amplifier 56 and resistors R2, R3 and R4. Other suitable oscillators that are usable with the subject electronic circuit include, but are not limited to, integrated circuit oscillators. The Schmidt trigger circuit functions to receive the voltage input signal $V_I$ from biosensor 70, convert that signal into an output signal $V_O$ in the form of an accurately-shaped, rectangular pulse waveform having an oscillation period proportional to the equivalent cell capacitance C of biosensor 70, and supplying the output signal $V_O$ as a digital input to microprocessor 52.

The Schmidt trigger circuit has an upper voltage ($V_H$) in the range from about 200 to 600 mV and a lower trigger voltage ($V_L$) in the range from about 0 to 500 mV. In a particular variation, the Schmidt trigger circuit has an upper trigger voltage $V_H$ of about 350 mV and a lower trigger voltage $V_L$ of about 250 mV. Accordingly, when there is no sample solution in the cell, R and C do not exist. When the circuit is powered up, C1 is initially discharged and therefore the input signal $V_I$ is below 250 mV. Under this condition, the output of operational amplifier 56 is at high voltage, i.e., approximates supply voltage $V_{CC}$, whereby C1 is then charged by the power supply voltage $V_{CC}$ across R1, and the output voltage $V_O$ remains at the supply voltage $V_{CC}$ which is in the range from about 1.8 to 5 V, and is more typically about 3 V. When the capacitor C1 charges, the input signal $V_I$ from terminal 72 increases until the voltage reaches above 350 mV. At this time, the output of the operational amplifier 56 goes to around zero volts whereby C1 is then discharged through resistor R1, and the output voltage $V_O$ remains at zero volts. Thus, the charging and discharging of the capacitance C1 causes the output voltage $V_O$ of the Schmidt trigger circuit to generate a rectangular oscillation. In the absence of a sample within biosensor 70, R1 and C1 determine the oscillation period or frequency of output voltage $V_O$. This latter oscillation period is determined by the following equation:

$$T_1 = R1C1\left(\ln\frac{V_H}{V_L} - \ln\frac{V_{cc} - V_L}{V_{cc} - V_H}\right) \quad (1)$$

where $T_1$ is the oscillation period, R1 and C1 are components discussed above, $V_H$ and $V_L$ are the respective high and low voltage levels of the Schmidt trigger circuit, and $V_{CC}$ is the supply voltage to the Schmidt trigger circuit. When a sample is applied to biosensor 70, the cell capacitance C is created in biosensor 70, producing an output voltage oscillation period determined by the following equation, choosing R1 such that R1<<R:

$$T_2 = R1(C1 + C)\left(\ln\frac{V_H}{V_L} - \ln\frac{V_{cc} - V_L}{V_{cc} - V_H}\right) \quad (2)$$

Accordingly, the differential or change ($\Delta T$) in the oscillation period of the output signal generated as between an input signal from biosensor 70 without a sample ($T_1$) and an input signal from biosensor 70 with a sample ($T_2$) is determined by the following equations:

$$\Delta T = T_2 - T_1 \quad (3)$$

$$\Delta T = R1C\left(\ln\frac{V_H}{V_L} - \ln\frac{V_{cc} - V_L}{V_{cc} - V_H}\right) \quad (4)$$

where $\Delta T$ is a linear function of the equivalent capacitance C of the biosensor's electrochemical cell. Therefore, by determining the oscillation period produced by the oscillation circuit, the equivalent cell capacitance can be determined.

Figure 5:
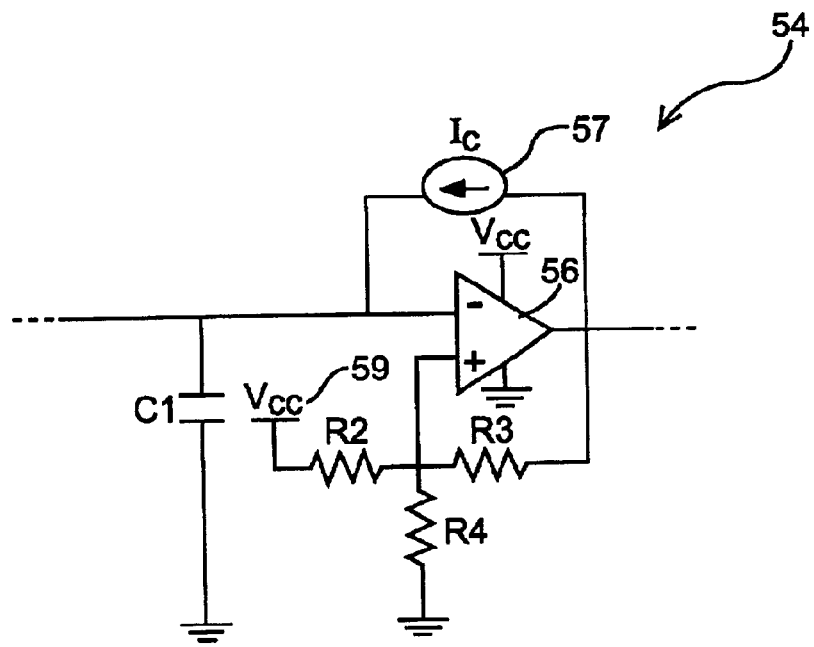
FIG. 5 is a schematic diagram of another embodiment of the oscillator circuit of the electronic circuit of FIG. 3.

Another embodiment of an oscillation circuit usable with the subject system is illustrated in FIG. 5 wherein resistor R1 has been replaced with a constant current source $I_C$ in order to control the amount of current applied to the sample. The direction of the current flow supplied by the current source is controlled by the output of operational amplifier 56, i.e., output signal $V_O$. When the output signal $V_O$ is high, the current source will supply current to the biosensor 70 via terminal 72 to charge the equivalent cell capacitance. The voltage across capacitor C1 will rise linearly rather than exponentially as in the embodiment of FIG. 3. When $V_I$ reaches around 350 mV, the output of the operational amplifier 56 changes the direction of the current source 57 and causes the cell capacitor C and circuit capacitor C1 to discharge and $V_I$ begins to decrease. This cycle will be repeated and a rectangular shape waveform is generated at the output of operational amplifier 56 ($V_O$).

With either oscillator circuit described above, the output signal $V_O$ is provided to microprocessor 52 via terminal 58. Since the output signal is either close to zero volts or power supply voltage it is directly connected to one of the available microprocessor I/O ports and there is no need to use an Analog to Digital (A/D) converter to convert the periodic signal into digital format. Microprocessor 52 is programmed to receive the output signal and derive and/or determine the factors or parameters of interest, e.g., equivalent cell capacitance, the surface area of the biosensor in contact with the biosensor, the volume of the biological sample, the compensation factor, etc.; and to control the timing of each of these functions. Microprocessor 52 may include a memory storage means for storing predetermined, pre-selected or calibrated data or information such as the total volume of the electrochemical cell, calibration parameters, operating temperature range, sample type information, sample detection information and the like which are necessary or useful for performing the steps and functions of the subject methods. Although a microprocessor has been described for purposes of storing and processing data in accordance with the principles of the present invention, those skilled in the art will recognize that other discrete electronic components may be collectively configured to achieve the objectives of the present invention.

The subject system may further include a display device or unit 80 for displaying selected empirical or symbolic data, information or outputs supplied by the control device or microprocessor. Such data, information or outputs may include, but are not limited to, measured or derived values of selected output signals and impedance factors, sample volume size, volume adequacy/inadequacy indicator icons, inadequate volume compensation factors, concentrations of analytes of interest, biological sample versus control sample indicator icons, calibration results, etc.

Those skilled in the relevant are will appreciate that the subject devices are usable with assay systems which do not comprise biosensors or electrochemical measurement devices of the type described above. Such other systems include, for example, an electrochemical cell having at least two electrodes and a redox reagent system having a fixed concentration of ions, wherein the electrodes are configured to be placed within a biological sample or environment having a fixed concentration of ions.

Methods of the Present Invention

Also provided by the subject invention are methods and protocols for determining the volume of biological sample provided for analyte concentration measurement and determining whether such volume is adequate to produce an accurate analyte concentration measurement. As mentioned above, a feature of the subject methods in determining sample volume is the determination of the equivalent capacitance of the cell, as well as the equivalent cell resistance. As such, the subject methods provide a more accurate measure of sample volume than that which has been achieved by the prior art.

Another feature of the subject methods in determining the equivalent cell capacitance and sample volume is to disregard certain characteristics or factors of the sampled solution or ambient conditions which either have no affect on the determination of the equivalent capacitance or otherwise strictly controlled so as not to have such an affect. Such factors which are controlled or independent of the equivalent capacitance include but are not limited to the concentration of ionic species, blood hematocrit, blood glucose concentration, environmental temperature, the blood donor, and sensor interferences typically found in blood, cell thickness and biosensor aging.

Another feature of the subject methods is to provide an oscillator operatively coupled to the electrochemical cell such that an oscillation is produced having a period proportional to the equivalent cell capacitance and deriving such capacitance from oscillation period.

Prior to practicing the subject methods, it is first necessary to obtain the biological sample to be measured and placing such sample within the test strip cell. This may be accomplished by first inserting the test strip into the test meter and then applying the sample to the test strip ("on-meter dosing"), or by first applying the sample to the test strip and then inserting the test strip into the test meter ("off-meter dosing"). The latter sequence is often preferred in hospital environments as it is less likely to cause cross-contamination within the meter. The measurement meter then detects that the biological sample has been introduced into the electrochemical cell (as disclosed in U.S. Pat. No. 6,193,873).

In practicing the subject methods, immediately after the deposit or transfer of a sample to within the biosensor 70, i.e., into the reaction area of the electrochemical cell of the test strip, is detected, an oscillator circuit is attached to the test strip thereby charging and discharging the electrochemical cell. The average of the voltage applied to the cell is a net DC voltage thereby causing the electrochemical cell equivalent capacitance to stabilize more rapidly. The average of the magnitude of the applied DC voltage has a value which meets glucose measurement requirements. The charging and discharging voltage across the cell capacitance (C) is then provided or supplied as an input signal $V_I$ to electronic circuit 50, specifically to oscillator circuit 54. From this input signal $V_I$, circuit 54 creates an oscillating voltage output ($V_O$) having a period proportional to that of the equivalent cell capacitance.

As is well known to those skilled in the art, the capacitance (Cap) of a simplified model of a capacitor, i.e., two parallel plates separated by an insulator or dielectric material, is represented by the following relationship:

$$Cap = \epsilon_o \epsilon_r \cdot A/d \quad (5)$$

where $\epsilon_O$ equals $8.85 \times 10^{-12}$ $N^{-1}$ $m^{-2}$ $C^2$, the permittivity or dielectric constant of free space, $\epsilon_r$ is the relative dielectric constant of the dielectric material, A is the surface area of the side of a plate in contact with the dielectric material and d is the separation distance between the dielectric-contacting surfaces of the plates. Thus, a characteristic of such a capacitor model is that its capacitance is directly proportional to the surface area of the plates. Therefore, by measuring the period of oscillator output signal, the equivalent cell capacitance is measured and since this capacitance is linearly proportional to the cell covered area, the covered cell area is obtained from oscillator period.

Upon a determination of the surface area of the electrode in contact with the sample solution, the volume ($V_S$) of the sample solution within the biosensor, i.e., within the reaction zone of the electrochemical cell, can then be determined according to the following equation:

$$V_S = A \cdot d \quad (6)$$

where d is the distance between the cell electrodes in a facing electrode configuration or the depth of the cell in a side-by-side electrode configuration.

A determination is then made as to whether the volume of the sample provided to the test strip is adequate to proceed with the analyte concentration measurement. The volume adequacy determination is made by comparing the calculated sample volume with the total volume of the electrochemical cell.

As is discussed above with respect to the systems of the present invention, certain parameters including but not limited to the value of the total cell volume, operating temperature range, proper test strip insertion into the meter, among other data (both static and dynamic) or parameters related to the particular electrochemical cell, are stored in the memory of a microprocessor, for example, upon calibration of the meter and other related components of the subject systems.

If the sample volume is determined to be adequate, measurement of the desired characteristic, e.g., an analyte concentration, is made, the results of which may be displayed on a display unit as described above with respect to the subject systems. On the other hand, if the sample volume is determined to be inadequate, i.e., too low, to provide an accurate measurement, the display unit may show a low volume icon.

As discussed above, certain embodiments of the subject methods include the additional function of compensating for an inadequate sample solution volume in order to make an accurate measurement of the selected characteristic, e.g., concentration of the targeted analyte(s), without having to redo the sampling and testing steps.

It is known in the art that the concentration of a selected analyte, such as glucose, of the biological sample within the cell is proportional to the Faradaic current ($I_F$) that is passed through the electrochemical cell when a DC voltage is applied, that the cell current is proportional to the cell surface area covered by the sample solution. As mentioned above, the inventor has determined that such surface area is proportional to the equivalent capacitance of the cell. Thus, the concentration of the selected analyte is proportional to the equivalent cell capacitance. By determining the equivalent cell capacitance when a sample solution is present and by knowing the capacitance of the cell when completely filled with a biological solution (determined by a calibration process), the compensation factor ($F_{cf}$) necessary to compensate for a low sample volume and to provide an accurate analyte concentration measurement can be determined according to the following equation:

$$F_{cf} = C_f / C_{pf} \quad (7)$$

where $C_f$ is the equivalent capacitance of the electrochemical cell when completely filled and $C_{pf}$ is the equivalent capacitance of the electrochemical cell containing the inadequate volume of biological sample. The corrected analyte concentration measurement (G) is then made with the appropriate compensation factor ($F_{cf}$) according to the following equation:

$$G = F_{cf} G_{pf} \quad (8)$$

where $G_{pf}$ is the analyte concentration calculated from the cell containing inadequate volume of biological sample. In being able to compensate for inadequately low sample volume, the subject methods avoid wasting test strips, decrease costs and reduce the time necessary for conducting the analyte measurement.

Thus, generally summarized in accordance with the above principles and discoveries, certain methods of the present invention include the steps of applying a DC voltage to the biosensor in order to charge the biosensor; converting the voltage signal generated as a result of such charging into an oscillating signal; determining the capacitance of the biosensor from this oscillating signal; determining the surface area of the portion of the biosensor in contact with the sample based on the determined capacitance; and then determining the volume of the sample within the biosensor based on the determined surface area.

The other subject methods may further include the step of measuring one or more physical or chemical characteristics of the biological sample, such as the concentration of one or more selected analytes, based on a determination that the sample volume is adequate. Still other subject methods may include compensating for an inadequate volume of a biological sample held within an electrochemical biosensor for measurement of at least one characteristic of the biological sample in order to accurately measure the value of the characteristic. Such compensation method includes determining the necessary compensation factor to compensate for an inadequate sample volume if such is determined, and thereafter compensating for the inadequate sample volume while measuring, for example, the concentration of a selected analyte present within the sample. The step of determining the necessary compensation factor includes determining the ratio of the equivalent capacitance of the biosensor when completely filled with the sample to the determined equivalent capacitance of the biosensor with the inadequate sample volume. The value of the equivalent capacitance of the biosensor when completely filled within said sample may be accessed from a memory storage means.

Experimental Examples

Figure 6:
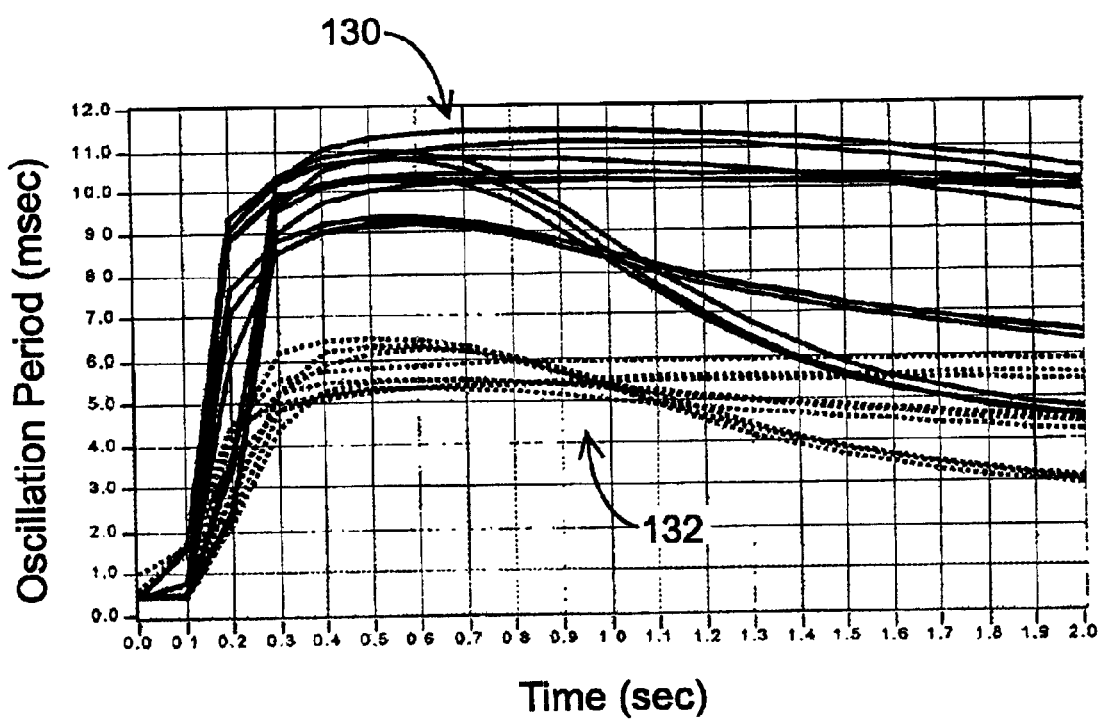
FIG. 6 is a graph depicting the relationship of the change in the oscillation period (y-axis) produced by an electrochemical cell over time (x-axis) after blood sample has been applied to the cell when the cell is completely filled and half filled, respectively, with a sampled solution.

The following results have been observed in connection with the present invention. FIG. 6 shows a comparison between the oscillation periods (y axis) over time (x axis) produced by a test strip having an adequate blood sample volume 130 and by a test strip having less than an adequate blood sample volume 132. The results of the experiment show there is a significant increase in the oscillation period when the test strip is completely filled with the sample solution. These empirical results are offered by way of illustration and not by way of limitation.

Kits

Also provided by the subject invention are kits for use in practicing the subject methods. The kits of the subject invention include a subject system including the electronic circuitry, as described above, or in the form of a meter or other automated instrument, as described above, for determining whether the volume of sample applied to a test strip is adequate enough to provide an accurate analyte concentration measurement to be made. In certain other kits, the subject systems also compensate for such inadequate volume when making an analyte concentration measurement. The kits may further include instructions for using the subject systems according to the subject methods with an electrochemical cell, in the form of a test strip or microneedle or the like, in the determination of the volume of a sampled solution or material held within the electrochemical cell. These instructions may be present on one or more of the packaging, a label insert, and the like.

It is evident from the above description that the features of the subject systems, devices and methods overcome many of the disadvantages of prior art techniques for determining the volume of a biological sample deposited on a test strip for electrochemical analyte concentration analysis, and provide certain advantages including, but not limited to, providing a very accurate means and technique for making such sample volume determination far more quickly and simply than prior art devices. Other advantages of the invention include the ability to compensate for an inadequate sample volume and proceed with the analyte concentration measurement without having to abort the testing procedure. As such, the subject invention represents a significant contribution to the field of fluid of biological sample volume determination and analyte concentration measurement.

The subject invention is shown and described herein in what is considered to be the most practical, and preferred embodiments. It is recognized, however, that departures may be made there from, which are within the scope of the invention, and that obvious modifications will occur to one skilled in the art upon reading this disclosure.

The specific devices and methods disclosed are considered to be illustrative and not restrictive. Modifications that come within the meaning and range of equivalents of the disclosed concepts, such as those that would readily occur to one skilled in the relevant art, are intended to be included within the scope of the appended claims.

What is claimed is:

1. An electronic circuit configured to be electrically coupled to an electrochemical cell for receiving a biological sample and having a capacitance created by said biological sample upon application of a voltage to said electrochemical cell, said circuit comprising:
an oscillation circuit configured to receive a voltage input signal resulting from the charging and discharging of the electrochemical cell and comprising a Schmidt trigger circuit for converting said voltage input signal to an oscillating voltage output signal proportional to the capacitance of the cell.

2. The electronic circuit of claim 1 further comprising means for deriving the value of the volume of said sample based on the cell capacitance.

3. The electronic circuit of claim 2 further comprising means for determining the adequacy of said volume for measurement of one or more analytes within the sample based on said oscillating voltage signal.

4. The electronic circuit of claim 3 further comprising means for compensating for said one or more analyte measurements when said volume is determined to be inadequate.

5. The electronic circuit of claim 1 further comprising a resistor electrically coupled to said Schmidt trigger circuit.

6. A kit for determining the volume of a biological sample deposited onto an electrochemical test strip comprising an electrochemical cell, said kit comprising at least one electronic circuit according to claim 1.

7. The kit of claim 6 further comprising an automated device within which said electronic circuit is integrally configured.

8. The kit of claim 7 further comprising instructions for using said electronic circuit and said automated device.

9. The electronic circuit of claim 1 further comprising a current supply electrically coupled to said Schmidt trigger circuit.

10. The electronic circuit of claim 1 wherein said capacitance is the equivalent capacitance of the cell.

11. The electronic circuit of claim 1 wherein the oscillation period of the oscillating voltage signal is directly proportional to the cell capacitance.

12. The electronic circuit of claim 1 wherein the oscillation frequency of the oscillating voltage signal is inversely proportional to the cell capacitance.

13. A system comprising:
a meter for receiving an electrochemical cell configured for receiving a biological sample and having a capacitance created by said biological sample when a voltage is applied to said electrochemical cell;
a DC voltage supply configured to be electrically connectable to said electrochemical cell for charging the electrochemical cell, wherein said cell capacitance is created; and
an electronic circuit integrally configured with said meter and configured to be electronically connectable to said electrochemical cell, said circuit comprising an oscillator circuit configured to receive a voltage input signal resulting from the charging and discharging of said electrochemical cell and configured to convert the voltage input signal to an oscillating voltage output signal, wherein the oscillation period of said oscillating voltage output signal is proportional to said cell capacitance.

14. The system of claim 13 wherein said electronic circuit further comprises a microprocessor electrically connected to said oscillator circuit and configured to determine the volume of the biological sample.

15. A method for determining the volume of a biological sample applied to an electrochemical cell, comprising:
providing the system of claim 13;

applying a DC voltage to said cell thereby charging said cell, wherein a capacitance is created within said cell, and generating a charged voltage as a result the capacitance; and converting the charged voltage to an oscillating voltage having a frequency proportional to the capacitance.

16. A kit for determining the volume of a biological sample within an electrochemical cell, comprising:

a system according to claim 13; and instructions for using said system.

17. The kit of claim 16 further including an automated device integral with said system configured to operatively receive and engage said electrochemical cell for determining one or more physical or chemical characteristics of the biological sample.

18. A system for determining the volume of a biological sample within an electrochemical cell having a surface area and a volume, comprising:

a voltage supply configured for applying a first voltage to said electrochemical cell;

means for measuring a second voltage generated by said cell when said first voltage is applied to said cell;

means for converting said second voltage into an oscillating voltage;

means for deriving the capacitance of said cell from said oscillating voltage;

means for deriving the volume of said biological sample from said cell capacitance.

19. The system of claim 18 further comprising means for determining whether said sample volume is adequate for making an accurate measurement of the concentration of one or more selected analytes within said biological sample.

20. The system of claim 19 further comprising:

means for measuring the concentration of one or more selected analytes within said biological sample; and means for compensating for said one or more selected analyte concentration measurements when said sample volume is determined to be inadequate.

21. The system of claim 20 further comprising means for displaying the measured concentration of one or more selected analytes within said biological sample.

22. The system of claim 18 wherein said means for deriving said volume comprises means for deriving the surface area of said cell covered by said biological sample from said cell capacitance and further comprises means for deriving said volume from said surface area.

23. A method for determining the volume of a biological sample applied to an electrochemical biosensor, comprising:

applying a direct current voltage to the biosensor thereby charging the biosensor, wherein a capacitance is created within the biosensor and a voltage is generated by charging the biosensor;

converting the voltage to an oscillating voltage having a period proportional to the capacitance;

determining the capacitance of the biosensor; and determining the volume of the sample from said capacitance.

24. The method of claim 23 further comprising determining whether said sample volume is adequate for measuring one or more selected characteristics of said sample.

25. The method of claim 24 further comprising:

determining the necessary compensation factor to compensate for said one or more selected characteristics measurements when said sample volume is inadequate;

measuring at least one characterstic of said sample; and compensating for the inadequate sample volume.

26. The method of claim 25 wherein the at least one characteristic of said sample is the concentration of one or more analytes present within said sample.

27. The method of claim 25 wherein said determining the necessary compensation factor comprises determining the ratio of the capacitance of the biosensor when completely filled with said sample to the capacitance of the biosensor filled with said inadequate sample volume.

28. The method of claim 24 wherein said volume determination comprises determining from said capacitance the surface area of the portion of said biosensor in contact with said biological sample and further comprising determining said volume from said surface area.

29. The method of claim 23 said determining said volume comprises determining the surface area of the portion of said biosensor in contact with said biological sample based on said determined capacitance.

30. The method of claim 29 wherein said electrochemical biosensor comprises at least two electrodes forming an electrochemical cell having a cell volume and wherein said determined surface area is a surface area of said at least two electrodes covered by said biological sample.

31. The method of claim 23 wherein an average of said direct current voltage is in the range from about 0 to 600 mV.

32. An electronic circuit configured to be electrically coupled to an electrochemical cell configured for receiving a biological sample, said circuit comprising:

means for applying a DC voltage to said electrochemical cell wherein, upon application of said DC voltage, said electrochemical cell generates a capacitance;

means for receiving a signal produced by said electrochemical cell; and means for converting said signal to an oscillating signal proportional to the capacitance of the cell.

33. The electronic circuit of claim 32 wherein said signal conversion means comprises a Schmidt trigger circuit.

34. The electronic circuit of claim 32 further comprising means for deriving the value of the volume of said sample based on the cell capacitance.

35. The electronic circuit of claim 34 further comprising means for determining the adequacy of said volume for measurement of one or more analytes within the sample based on said oscillating signal.

36. The electronic circuit of claim 35 further comprising means for compensating for said one or more analyte measurements when said volume is determined to be inadequate.

37. The electronic circuit of claim 32 wherein the oscillation period of said oscillating signal is proportional to the cell capacitance.

38. The electronic circuit of claim 32 wherein the oscillation frequency of said oscillating signal is inversely proportional to the cell capacitance.

39. An electronic circuit configured to be electrically coupled to an electrochemical cell for receiving a biological sample and having a capacitance created by said biological sample upon application of a voltage to said electrochemical cell, said circuit comprising:

an oscillation circuit configured to receive a voltage input signal resulting from the charging and discharging of the electrochemical cell and comprising a comparator circuit for converting said voltage input signal to an oscillating voltage output signal proportional to the capacitance of the cell.

40. The electronic circuit of claim 39 further comprising means for deriving the value of the volume of said sample based on the cell capacitance.

41. The electronic circuit of claim 40 further comprising means for determining the adequacy of said volume for measurement of one or more analytes within the sample based on said oscillating voltage signal.

42. The electronic circuit of claim 41 further comprising means for compensating for said one or more analyte measurements when said volume is determined to be inadequate.

43. The electronic circuit of claim 39 further comprising a resistor electrically coupled to said comparator circuit.

44. The electronic circuit of claim 39 further comprising a current supply electrically coupled to said comparator circuit.

45. The electronic circuit of claim 39 wherein said capacitance is the equivalent capacitance of the cell.

46. The electronic circuit of claim 39 wherein the oscillation period of the oscillating voltage signal is directly proportional to the cell capacitance.

47. The electronic circuit of claim 39 wherein the oscillation frequency of the oscillating voltage signal is inversely proportional to the cell capacitance.

* * * * *